(12) United States Patent
Dey et al.

(10) Patent No.: US 8,128,859 B2
(45) Date of Patent: Mar. 6, 2012

(54) METHOD FOR FORMING PRE-MADE POUCHES

(75) Inventors: Clifford Dey, Riegelsville, PA (US);
Dwayne Looney, Flemington, NJ (US);
Michael Pohle, Flemington, NJ (US);
Robert Cerwin, Pipersville, NJ (US)

(73) Assignee: Ethicon, Inc., Somerville, NJ (US)

( * ) Notice: Subject to any disclaimer, the term of this patent is extended or adjusted under 35 U.S.C. 154(b) by 30 days.

(21) Appl. No.: 12/849,380

(22) Filed: Aug. 3, 2010

(65) Prior Publication Data
US 2010/0314805 A1 Dec. 16, 2010

Related U.S. Application Data

(62) Division of application No. 12/164,306, filed on Jun. 30, 2008.

(51) Int. Cl.
*B29C 49/00* (2006.01)

(52) U.S. Cl. ..... 264/523; 264/572; 425/522; 425/387.1; 425/397; 425/400; 425/411; 425/395

(58) Field of Classification Search ............... 425/387.1, 425/450.1, 411, 395, 397, 400, 522; 264/523, 264/527
See application file for complete search history.

(56) References Cited

U.S. PATENT DOCUMENTS

| | | |
|---|---|---|
| 3,000,157 A | 9/1961 | Ollier et al. |
| 3,299,603 A | 1/1967 | Shaw |
| 3,726,057 A | 4/1973 | Kemble |
| 3,728,839 A | 4/1973 | Glick |
| 3,808,772 A | 5/1974 | Turtschan |
| 3,815,315 A | 6/1974 | Glick |
| 3,926,311 A | 12/1975 | Laske |
| 3,979,877 A | 9/1976 | Vetter |
| 4,069,645 A | 1/1978 | Vetter |
| 4,141,196 A | 2/1979 | Blanding |
| 4,224,779 A | 9/1980 | Guedet |
| 4,299,075 A | 11/1981 | Gram |
| 4,329,829 A | 5/1982 | Torterotot |
| 4,482,053 A | 11/1984 | Alpern et al. |
| 4,503,656 A | 3/1985 | Hautemont |
| 4,603,538 A | 8/1986 | Shave |
| 4,627,221 A | 12/1986 | Buchner |
| 4,636,391 A | 1/1987 | Pike |
| 4,731,980 A | 3/1988 | Worden et al. |
| 4,817,366 A | 4/1989 | Konzal et al. |
| 5,178,277 A | 1/1993 | Brown et al. |
| 5,217,772 A | 6/1993 | Brown et al. |
| 5,220,769 A | 6/1993 | Brown et al. |
| 5,493,845 A | 2/1996 | Adolf et al. |
| 5,590,778 A | 1/1997 | Dutchik |
| 5,623,810 A | 4/1997 | Dey et al. |
| 5,669,208 A | 9/1997 | Tabaroni et al. |
| 5,868,244 A | 2/1999 | Ivanov et al. |
| 6,096,358 A | 8/2000 | Murdick et al. |
| 6,718,735 B2 | 4/2004 | Lewis, Jr. et al. |
| 6,779,318 B2 | 8/2004 | Wang |
| 2006/0010841 A1 | 1/2006 | Trezza, II et al. |

FOREIGN PATENT DOCUMENTS

| | | |
|---|---|---|
| CA | 2169728 C | 2/1995 |
| DE | 4243325 A1 | 6/1994 |

*Primary Examiner* — Christina Johnson
*Assistant Examiner* — Saeed Huda
(74) *Attorney, Agent, or Firm* — E. Richard Skula

(57) ABSTRACT

An apparatus and method for forming cavities in pouches. The packages are used for packaging sterile medical products. The apparatus has a frame and a tongue plate member. A pouch is placed onto the tongue plate member to form a cavity into at least one side of the pouch.

1 Claim, 11 Drawing Sheets

METHOD FOR FORMING PRE-MADE POUCHES

CROSS REFERENCE TO RELATED APPLICATION

This application is a divisional of application Ser. No. 12/164,306, filed on Jun. 30, 2008.

FIELD OF THE INVENTION

The field to which this invention relates is packaging machinery and processes, in particular, packaging and machinery for forming medical device packages.

BACKGROUND OF THE INVENTION

Pouch-type packaging is very flexible and adaptable to a variety of medical products, including medical devices. An example of a pouch-type package without formed cavities is two flat similarly sized rectangular sheets of material aligned and placed directly over one another and sealed together along three of their four edges. The fourth edge is left open to form the pouch and provide an entrance opening into the interior of the pouch. The fourth side may be sealed after a product such as a medical device is placed inside the pouch (often referred to the filling process). This operation is not typically conducted in a sterile environment, although it may be. Therefore, it is then desirable to sterilize the product that is now contained within the pouch, along with the interior of the pouch, in order to provide a sterile product. Various types of sterilization processes are known in the art to sterilize medical products, including gas sterilization, autoclaving, gas plasma sterilization, radiation and other conventional processes. When utilizing a gas sterilant process such as ethylene oxide, one of the flat rectangular sheets may include a gas permeable barrier such as a TYVEK® sheet. Sterilization gases can penetrate the gas permeable barrier to sterilize the product inside the sealed pouch. Once the sterilization process is completed, a fifth seal may be made to isolate the product from the gas permeable section of the sealed pouch. Following this operation, the portion of the pouch that contains the gas permeable barrier is removed. When using two sheets which are not gas permeable, the package is sealed along the fourth edge after ethylene oxide sterilization in a clean room.

Forming is defined as the process of creating a cavity in one or both sheets of material used to form the pouch to accommodate a product to be packaged. Formed cavities are especially useful in pouch-type packages because they allow larger products to be housed or filled within a given size pouch without the formation of wrinkles. Wrinkle formation in one or both sheets is typical of a non-formed pouch package. These wrinkles can be eliminated if one or both sheets have pockets formed in them to accommodate the intended product. There may be disadvantages associated with such wrinkles, including channels and unsealed sections or areas which result is a loss of sterility and barrier to moisture and oxygen. . . .

Flat pouches are typically made form roll stock on seal and cut equipment. Pouches may be formed from two rolls of laminate foil material such rolls of heat sealable packaging materials. These materials can be foil laminates, films, heat sealable papers or spun bonded plastics. Thermo forming is performed on films while cold pressure forming is typical for foil laminates Forming process typically are performed on conventional form/fill/seal equipment. These types of systems can easily fabricate numerous flat pouches or envelopes that may be later transported to subsequent operations for filling and final sealing as described above. As previously mentioned, it is often desirable to have a formed cavity in one or both sides of the pouch. This is accomplished by forming a cavity in one (or both) sheet(s), placing the product into a cavity, and then placing and sealing the two sheets together. Where cavities are formed in both sheets, care must be taken to assure accurate registration and alignment of the sheets before they are sealed. This type of process may be automated as a continuous process wherein package formation, filling with product, and sealing are all conducted in a continuous manner. This type of system works well for most products that are not sterile, however, it does not work well for sterile product that needs to be aseptically filled and sealed into the pouch.

Aseptic packaging processes and equipment are known in the art. Aseptically filling and sealing a product into a package is typically conducted in an aseptic environment. Such environments are difficult and costly to fabricate on a scale large enough to accommodate form, fill, and seal systems as described above. One approach used for aseptic packaging is to manufacture pouches in a non-sterile environment, stack them, sterilize them, and then transfer them into an aseptic environment for the filling and sealing operation. This process works well with pouches that are not formed. However, formed pouches present some additional challenges. Formed pouches, when stacked take up much more space and therefore fewer pouches can be accommodated in each stack. Even if gently stacked, the pouches are typically easily damaged during the sterilization process and subsequent transport into an aseptic environment. Damage may include wrinkle formation and hole formation. Wrinkled or unsupported surfaces present yet additional challenges when the application of labels on the outer package surface is desired.

Therefore, there is a need for novel packaging processes and machines for making pouches having formed cavities adapted for use in an aseptic environment.

SUMMARY OF THE INVENTION

Accordingly, a novel apparatus for manufacturing pouches having cavities is disclosed. The apparatus has a frame. A bottom or lower clamp plate member is slidably mounted to the frame. The bottom plate member has a top side and a bottom side. A top die plate member is slidably mounted to the frame. The top plate member has a top side and a bottom side. First and second actuators are mounted to the frame for moving the bottom plate member and the top plate member toward each other. There is a die member extending from the bottom of the top plate member. Optionally, a die member extends from the top side of the bottom plate member. The die member has a cavity. The apparatus also has a tongue plate member plate having a first end and a second end. The second end of the tongue member is fixedly mounted to the frame between the top plate member and the bottom plate member such that the tongue member extends between the top plate and the bottom plate. The tongue member has a fluid passage having a first opening, and a second opening through the top side. The first and second openings are in communication with the fluid passage. Optionally, the tongue member has an opening on the bottom side.

Another aspect of the present invention is a method of manufacturing a pouch having a cavity using the above described apparatus. In this method, a pouch is provided. The pouch has two sheets aligned and sealed along three sides such that the pouch has an unsealed side and an opening into an interior. An apparatus of the present invention is provided. The apparatus has a frame. A bottom or clamp plate member is slidably mounted to the frame. The bottom plate member has a top side and a bottom side. A top die plate member is slidably mounted to the frame. The top plate member has a top side and a bottom side. First and second actuators are mounted to the frame for moving the bottom plate member and the top plate member toward each other. There is a die member extending from the bottom of the top plate member. The die member has a cavity. The apparatus also has a tongue plate member having a first end and a second end. The second end of the tongue member is fixedly mounted to the frame between the top plate and the bottom plate such that the tongue member extends between the top plate member and the bottom plate member. The tongue member has a fluid passage having a first opening, and a second opening through the top side. The first and second openings are in communication with the fluid passage. The pouch is placed over the tongue member, such that a section of the tongue member is contained within the interior of the pouch. The top and bottom plate members are moved toward each other such that the die contacts the top of the pouch and the bottom plate member contacts the bottom of the pouch against the bottom and top surfaces of the tongue member, respectively. A pressurized fluid is caused to move into the fluid passage of the tongue and out through the second opening, thereby causing a section of the top sheet of the pouch to be forced into the cavity of the die, and thereby forming a cavity in the top sheet. The top and bottom plate members are away from the tongue member, and, the pouch having a formed cavity is removed from the tongue member.

These and other aspects and advantages of the present invention will become more apparent from the following description and accompanying drawings.

DETAILED DESCRIPTION OF THE INVENTION

The pouches useful in the practice of the present invention are made from sheets of flat materials know in this art useful for forming pouch packages for sterile medical products, particularly medical devices. Typically, each sheet is made from a conventional foil or a foil laminate made from materials such as aluminum foil, polymer sheets, coatings and the like, e.g., polyester/foil/polyethylene heat seal coating. Optionally, a first sheet is made from the previously described foil laminate, and the second sheet is made from a conventional gas-permeable polymeric material such as TYVEK spun polytetraflouroethane, heat seal coated medical grade paper, and the like. Optionally the second sheet can be made from a metal foil laminate and can have a vent opening with a section of a gas permeable polymeric sheet affixed over the vent opening. In addition, the second sheet is optionally a conventional polymeric gas impermeable sheet such as, polyethylene, polyester, halogenated films such as Aclar and PVC, and the like. The sheets of materials are bonded together via a peripheral seal in a conventional manners including heat sealing, ultrasonic welding, radiofrequency, microwave, gluing and the like. Packages using pouches and methods of packaging sterile medical devices are disclosed in the following U.S. patents, which are incorporated by reference: U.S. Pat. No. 5,868,244; U.S. Pat. No. 5,732,529; U.S. Pat. No. 5,623,810; and, U.S. Pat. No. 4,482,053.

Figure 1:
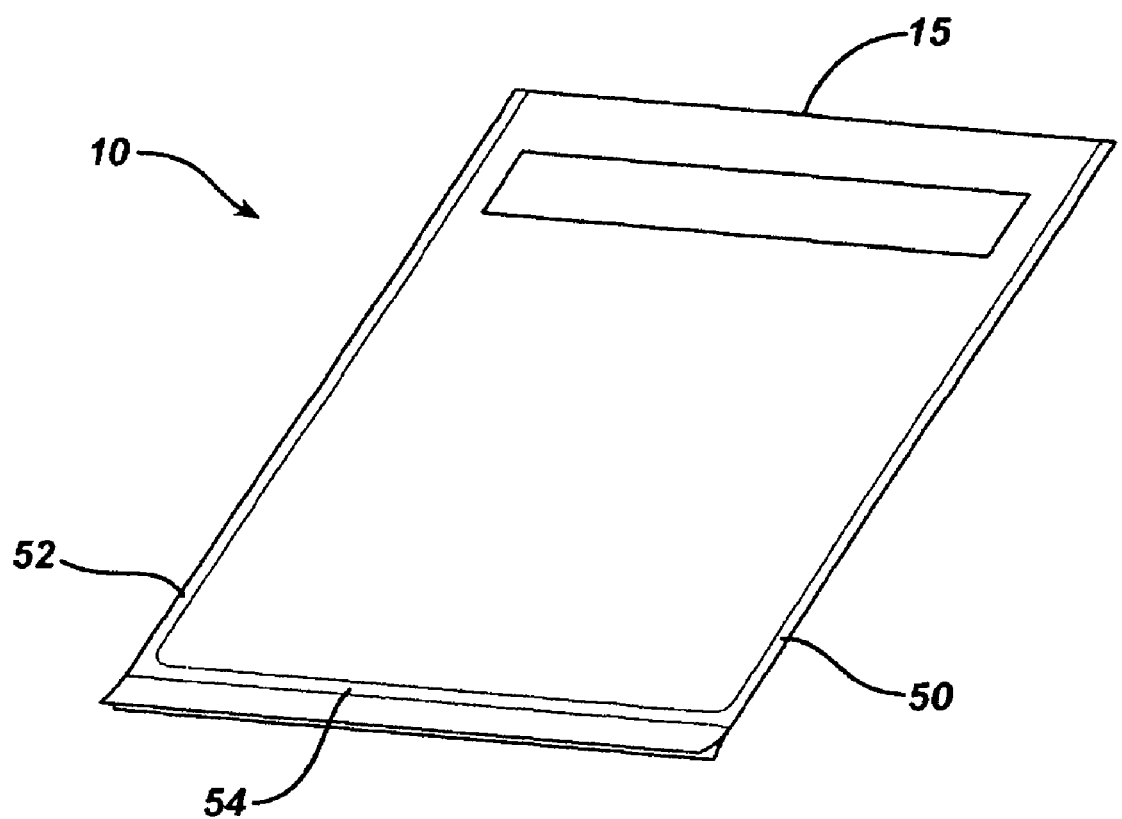
FIG. 1 is a perspective view of a pouch of the present invention prior to processing to form a cavity.
Figure 2A:
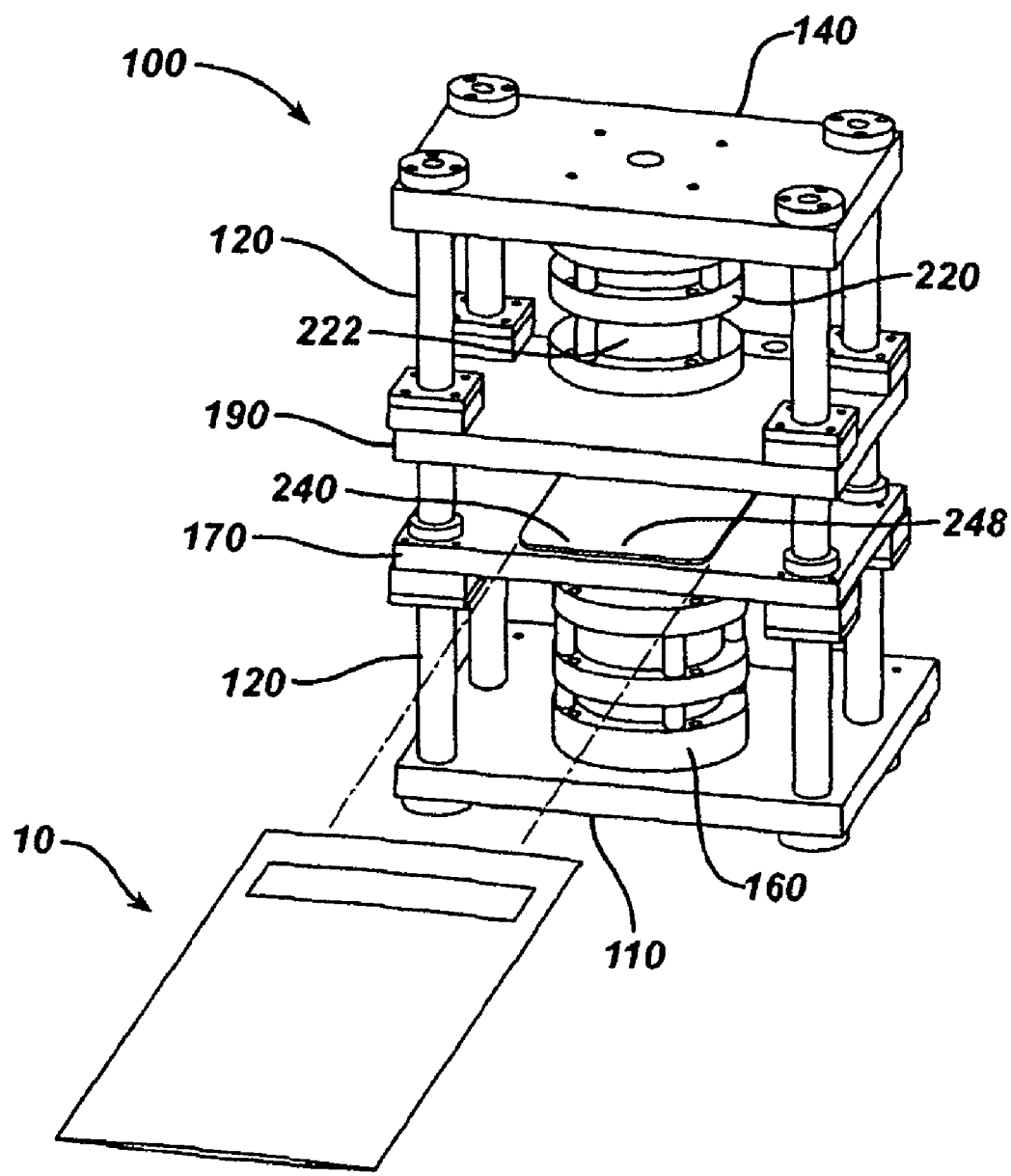
FIG. 2a is a perspective view of a machine of the present invention useful to manufacture pre-formed pouches illustrating the front of the machine.
Figure 2B:
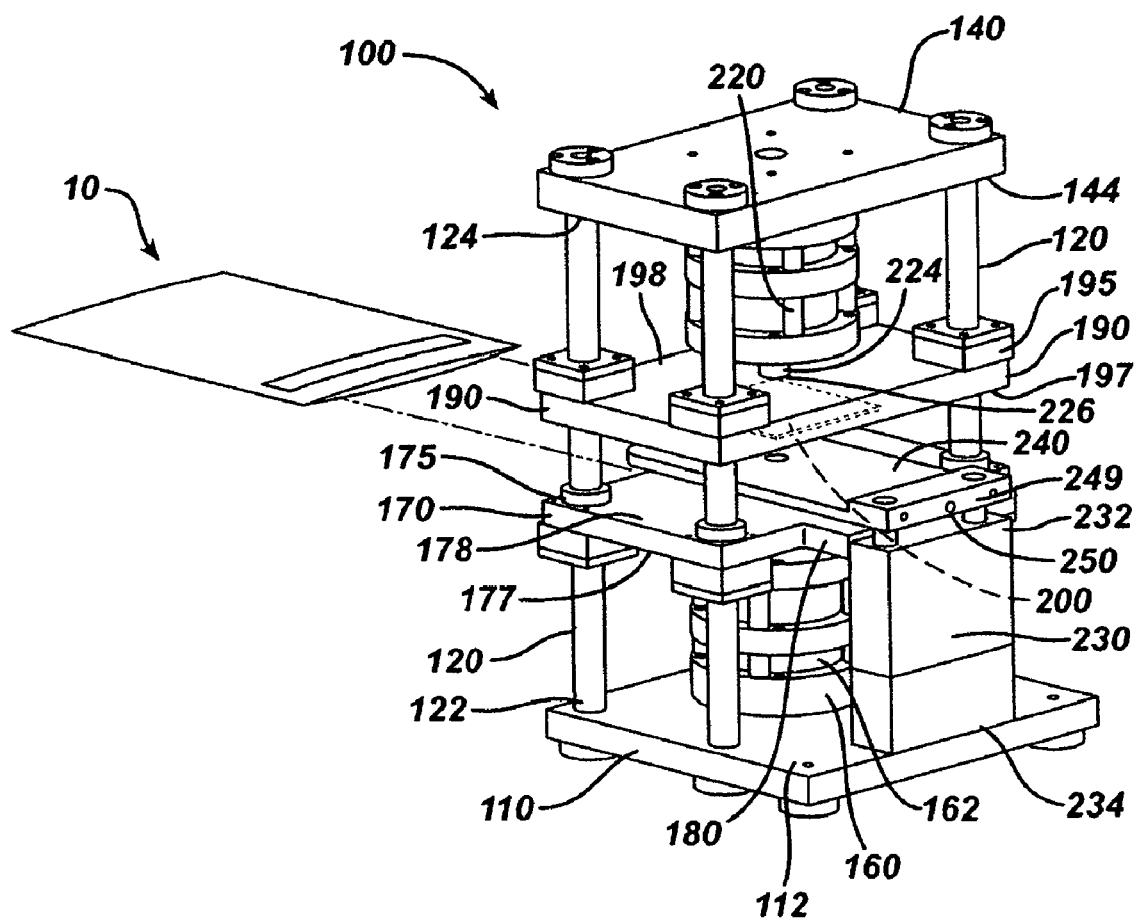
FIG. 2b is a perspective view of a machine of FIG. 2a illustrating the back of the machine.
Figure 3A:
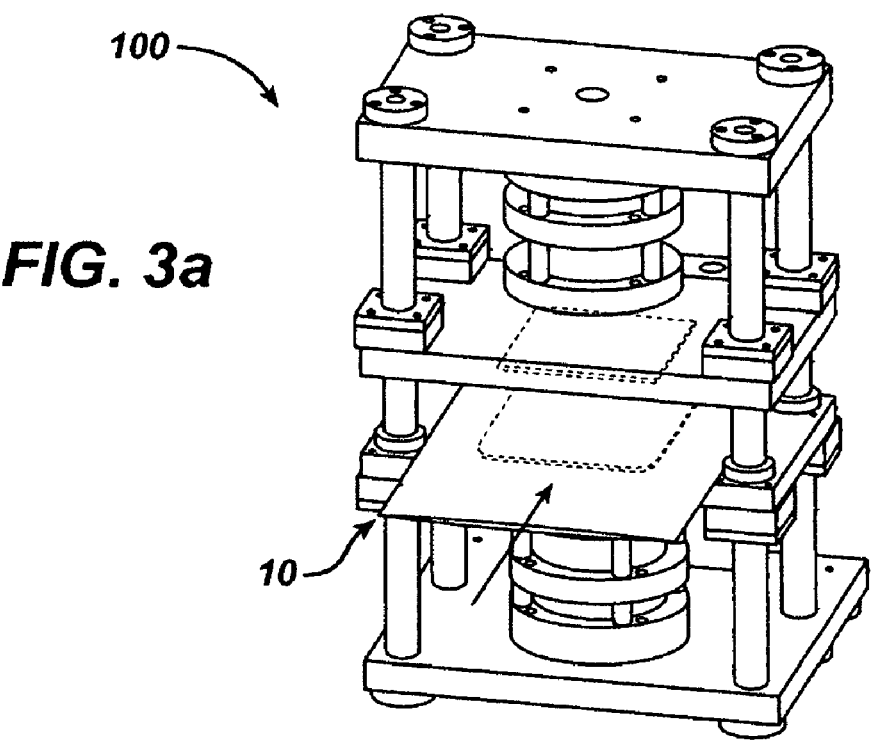
FIGS. 3a and 3b are perspective views of the machine of FIG. 1 illustrating an unformed pouch being inserted over the tongue member prior to forming a cavity in the pouch
Figure 3B:
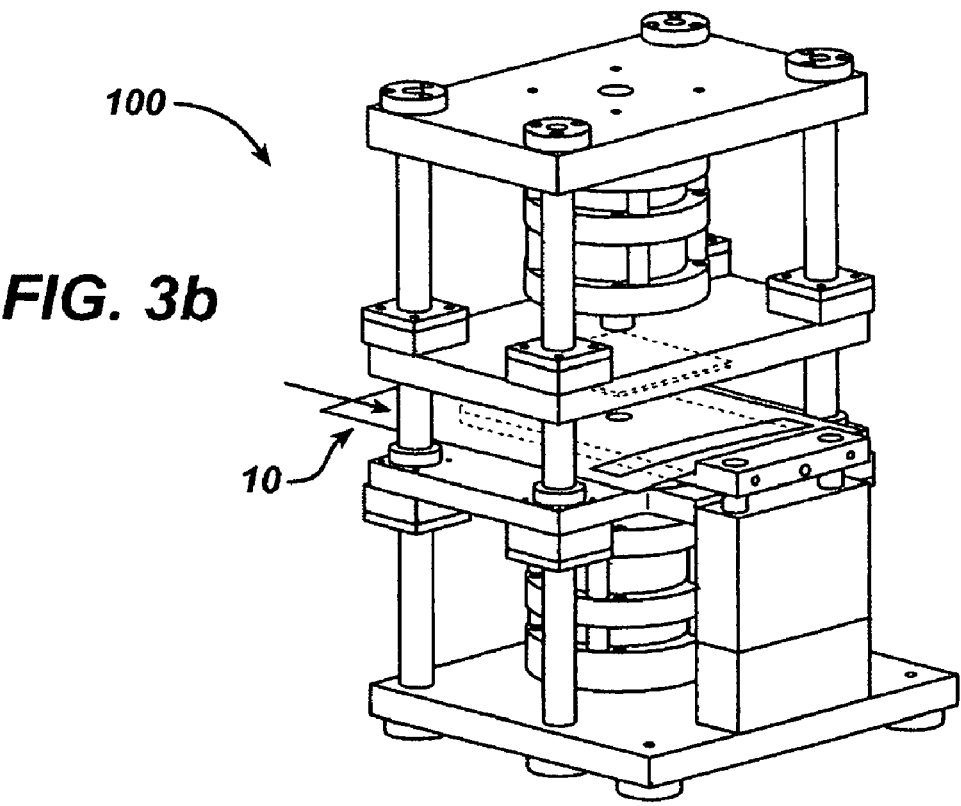
Figure 4A:
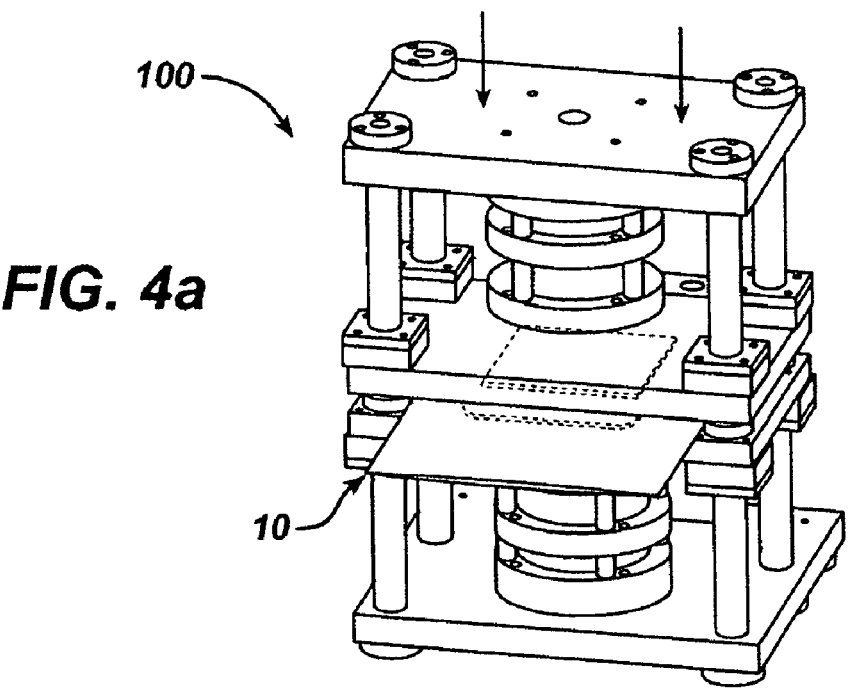
FIGS. 4a and 4b are perspective views of the machine of FIG. 1 illustrating the plate members closed about the tongue member and pouch for the cavity forming step.
Figure 4B:
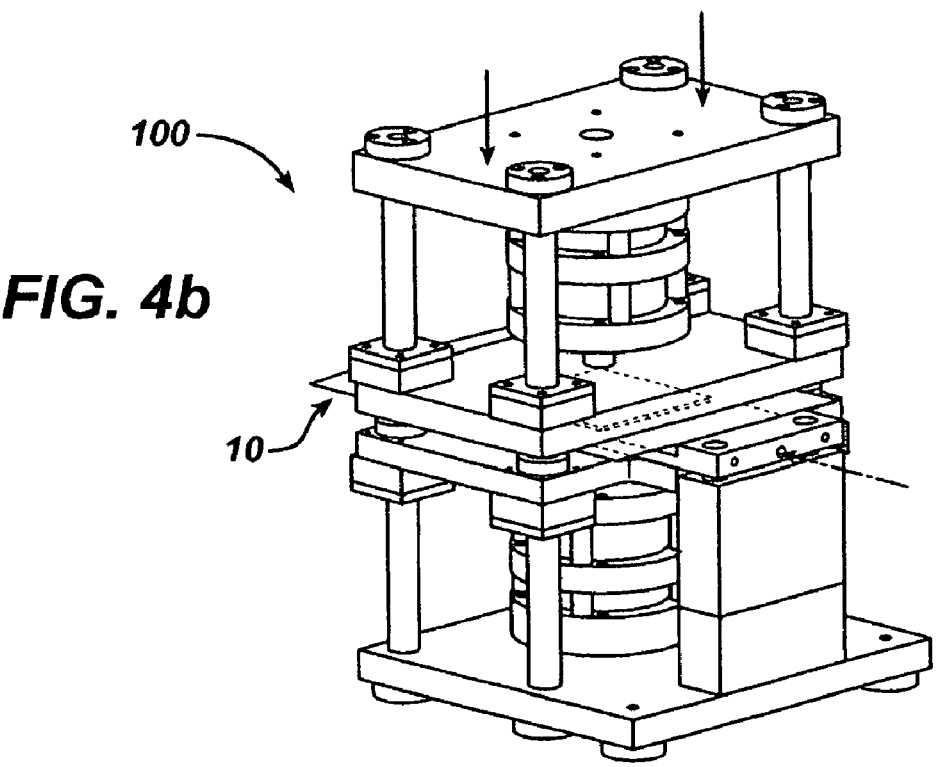
Figure 5A:
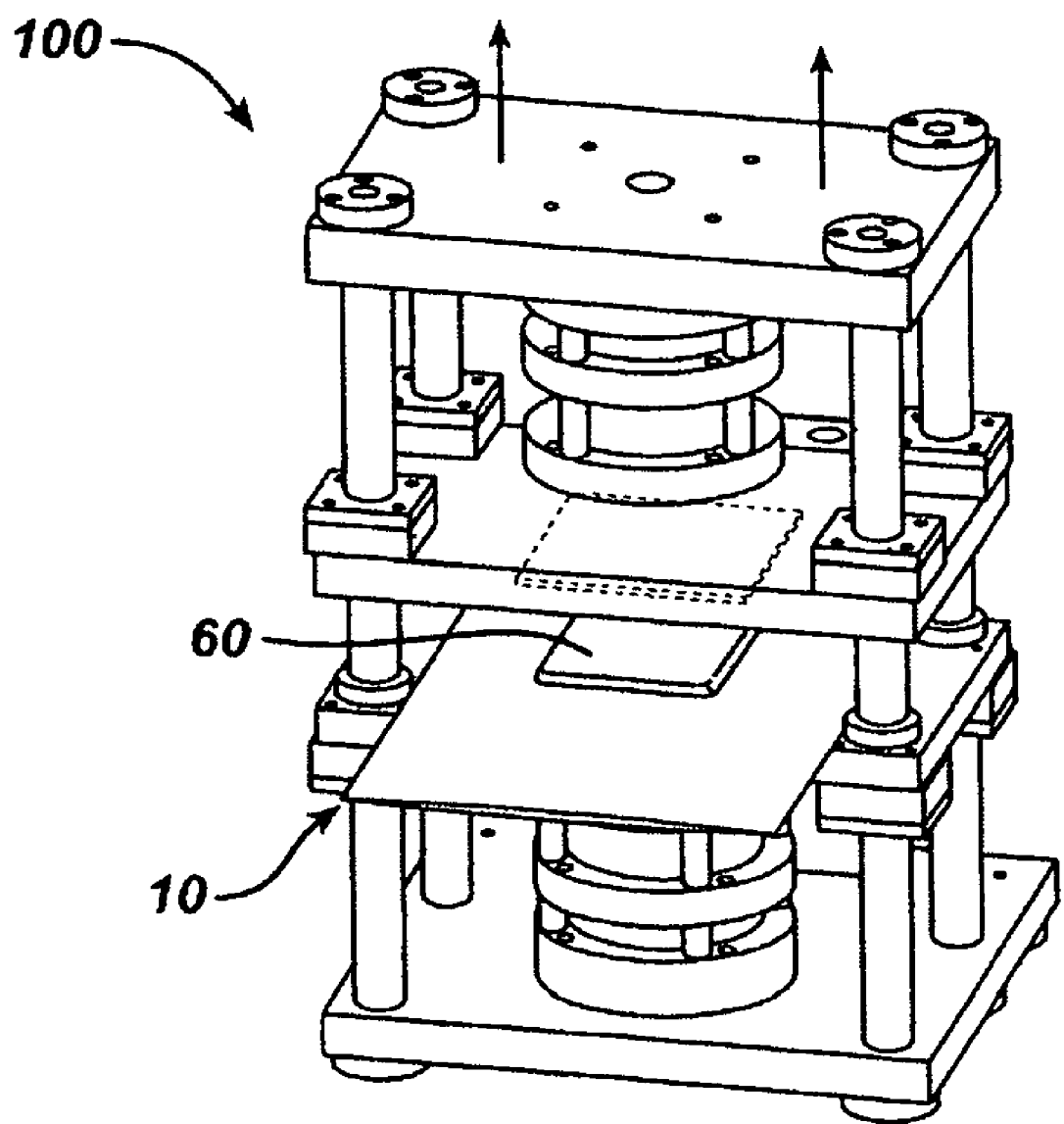
FIGS. 5a and 5b are perspective views of the machine of FIG. 1 illustrating the plate members opened after the cavity forming step and illustrating a cavity formed in the pouch prior to removal from the tongue member and the machine.
Figure 5B:
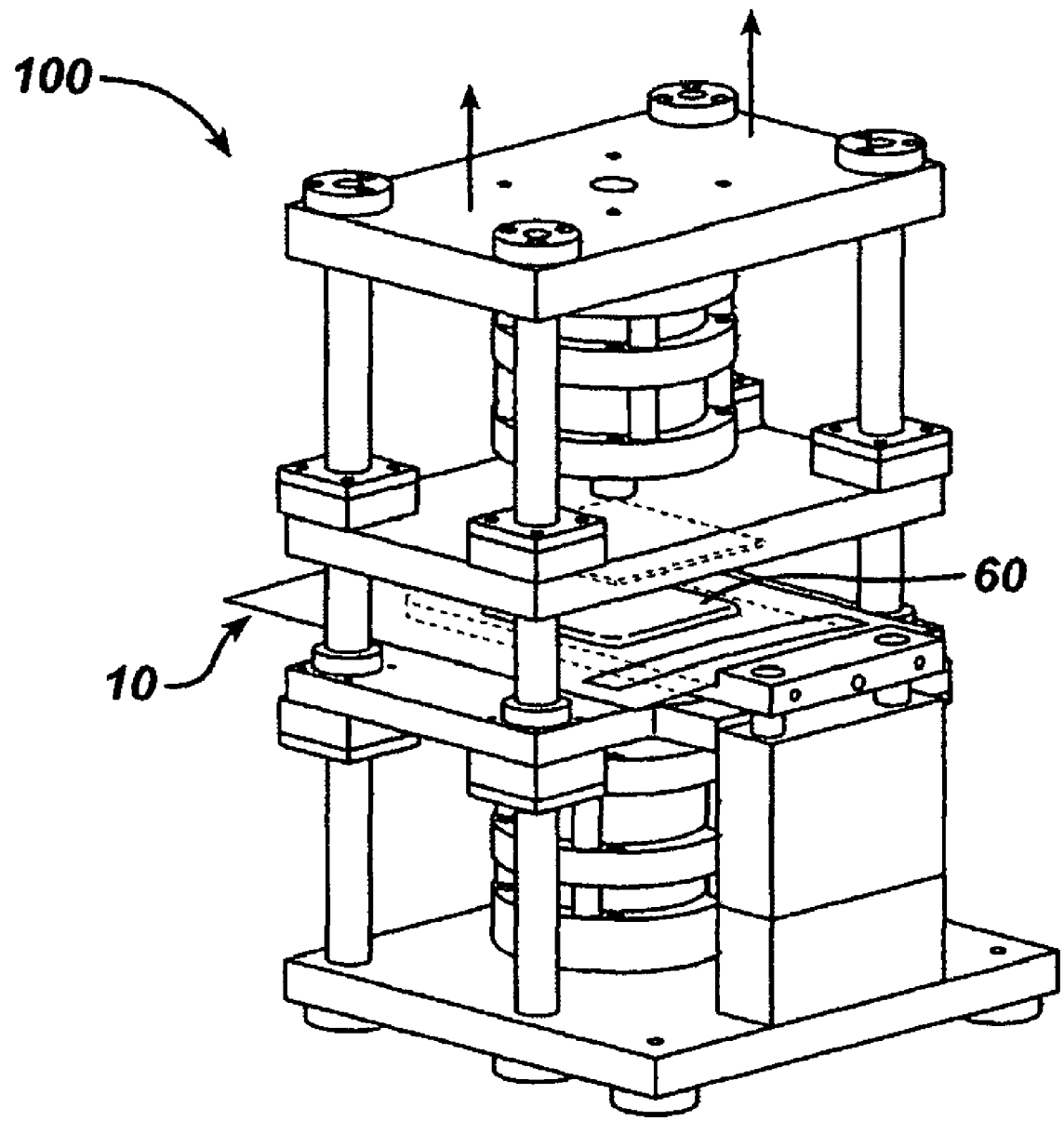
Figure 6:
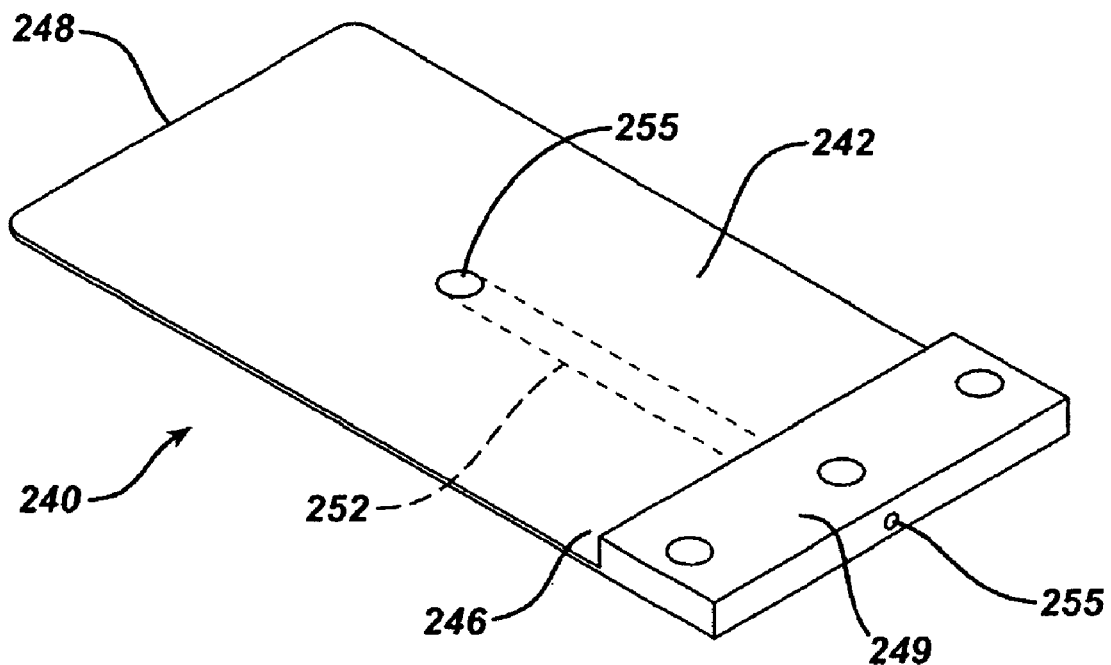
FIG. 6 is a perspective view of a tongue member used in the machine and process of the present invention
Figure 7:
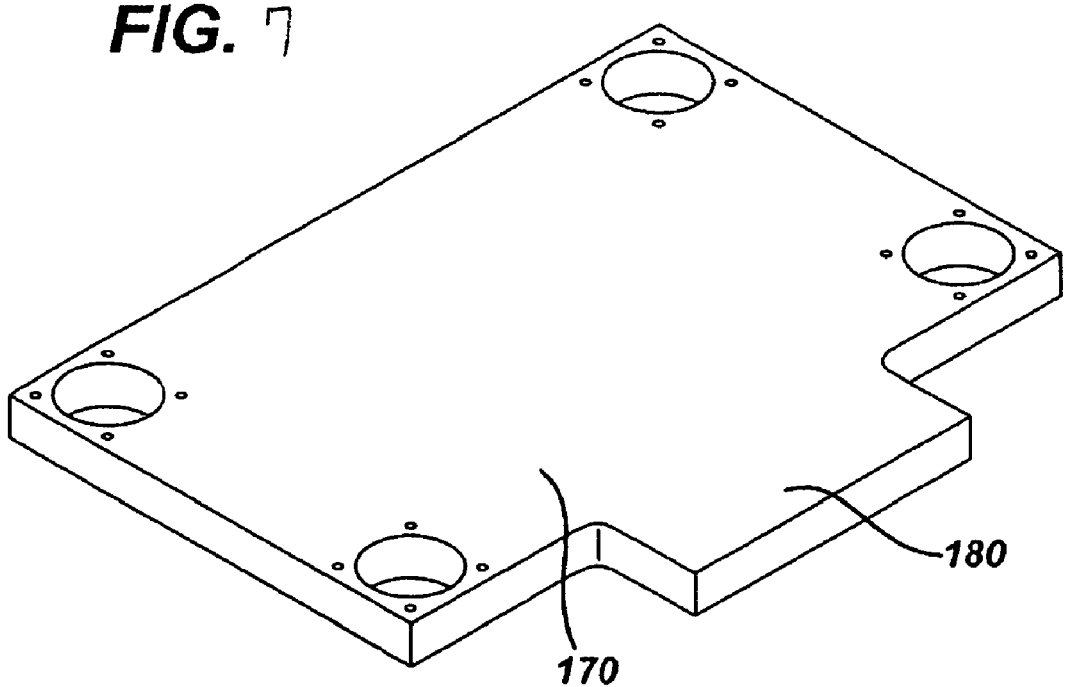
FIG. 7 is a perspective view of a lower clamp plate member of the machine of the present invention.
Figure 8:
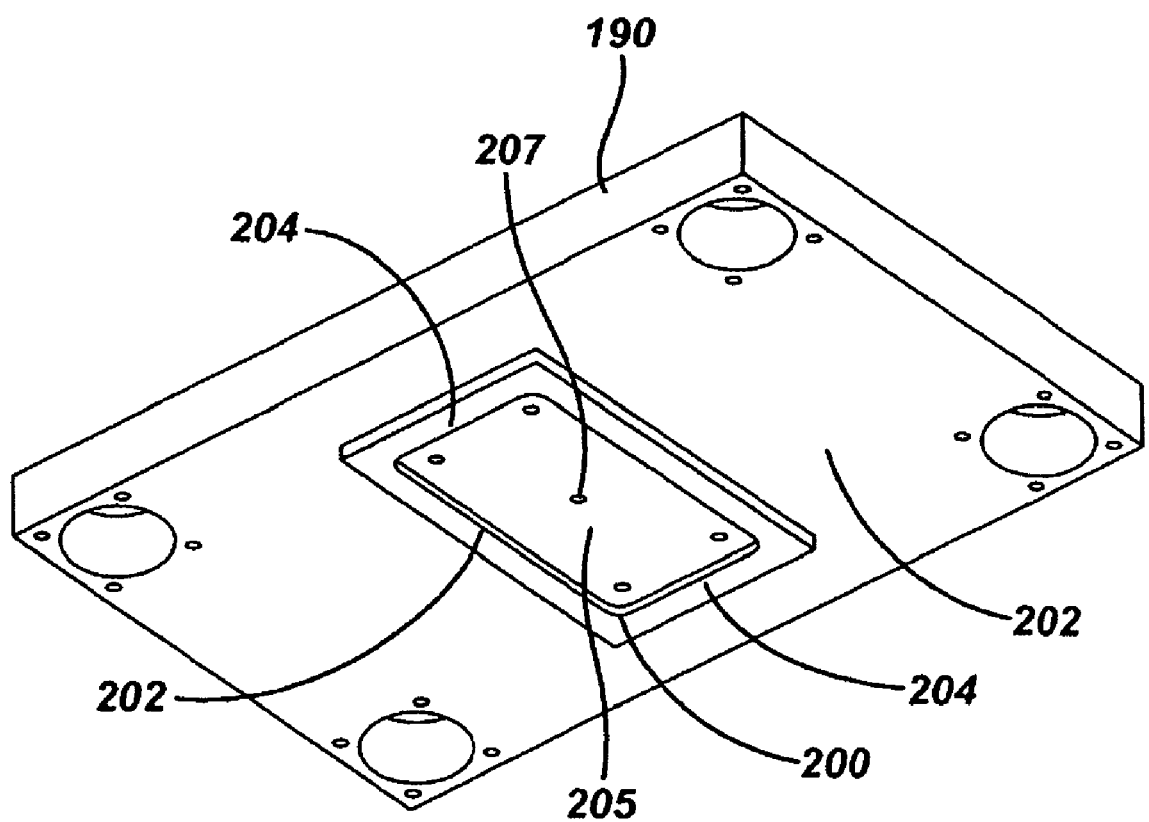
FIG. 8 is a perspective view of a cavity plate member of the machine of the present invention.
Figure 9:
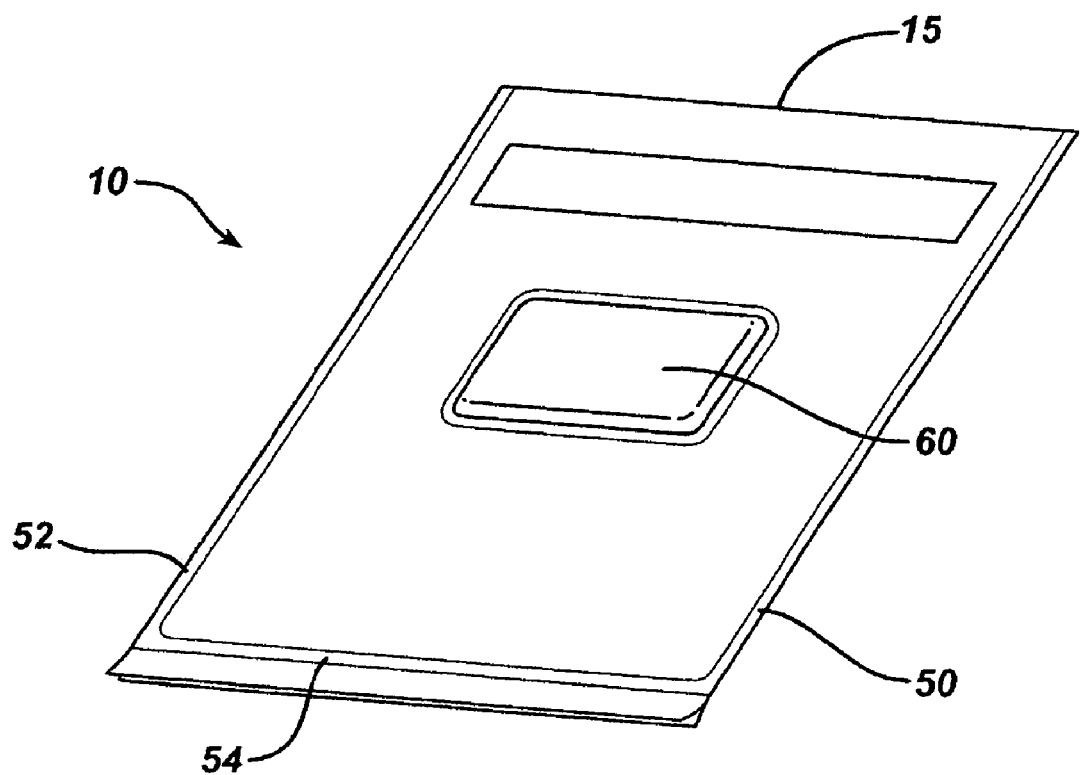
FIG. 9 is a perspective view of the pouch of FIG. 1 after it has been processed using the machine and process of the present invention to form a cavity therein.
Figure 10:
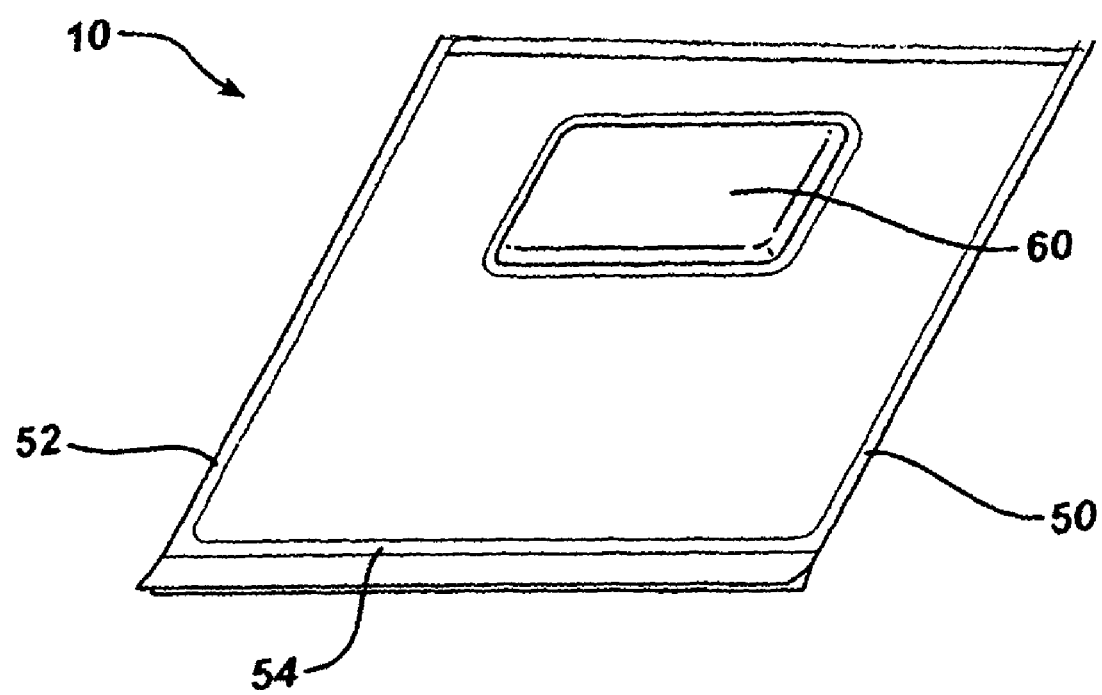
FIG. 10 is a perspective view of the pouch of FIG. 9 after it has been filled with a medical device and sterilized.

A flat pouch 10 useful in the practice of the process of present invention is illustrated in FIG. 1. The pouch 10 is seen to have top foil sheet 30 and bottom foil sheet 40. The pouch 10 is seen to be sealed about the periphery of three sides using a conventional sealing process such as heat sealing or equivalent processes to form seal 50. The seal 50 has lateral sides 52 and bottom side 54. The pouch 10 has open top side 15 with entrance opening 20 to interior cavity 22. The pouch 10 is seen to have optional gas vent 12. Referring to FIG. 9, the pouch 10 is seen after processing using the equipment and process of the present invention to have a cavity 60 formed into bottom sheet 30. A sterile package 10 of the present invention after filling with a medical device 70 and subsequent sealing (and conventional gas sterilization) is seen in FIG. 10. The package 10 is seen to have top side 15 sealed by top seal 56, with the section of the package containing optional vent 12 removed in a conventional manner such as by cutting. If the pouch 10 does not have a gas vent, it may be filled with a medical device, sterilized with a conventional gas process, and then aseptically sealed. Optionally, other types of sterilization processes may be used including conventional plasma, radiation and autoclaving sterilization processes, and in the case of radiation and autoclaving, the pouch of the present invention having a cavity may be hermetically sealed prior to the sterilization process.

A novel package forming machine 100 of the present invention is illustrated in FIGS. 2-8. Machine 100 is seen to have bottom base member 110. Extending upwardly from the top 112 of the base member 100 are the guideposts 120, having bottoms 122 and tops 124. Mounted to the tops 124 of the posts 120 is the top plate member 140. The plate members 110 and 140 may be mounted to the bottoms 122 and 124 of posts 120 in a conventional manner such as screw head cap screws, nuts, welding, fittings, and the like. The lower cylinder actuator 160 is seen to be mounted to the top 112 of base member 110. Cylinder actuator 160 is seen to have cylinder 162 and actuator rod 164 having end 166. The lower clamp plate or bottom plate member 170 is slidably mounted to the guideposts 120 through guidepost openings 175. Plate member 170 has bottom 177 and top 178. Extending from one side of the plate member 170 is the extension member 180. The end 164 of actuator rod 164 is connected to the bottom side 177 of plate member 170. Upper cavity plate member 190 is seen to be slidably mounted to the guideposts 120 through the guidepost openings 195. Plate member 190 has top side 198 and bottom side 197. Mounted to the bottom 144 of top plate member 140 is the actuator cylinder 220. Actuator cylinder 220 has cylinder 222 and actuator rod 224 having end 226. End 226 of actuator cylinder 220 is mounted to the top 198 of cavity plate member 190. Extending downwardly from the bottom side 197 of cavity plate member 190 is the die member 200. Die member 200 is seen to have raised opposed sides 202 and 204. The sides 202 and 204 extend above bottom 205 and surround cavity 207 formed by the sides 202 and 204 and the bottom 205. Extending up from the top 112 of bottom plate 110 is the mounting tower 230. Tower 230 has top 232 and bottom 234. The forming tongue member 240 is seen to have top 242 and bottom 244, and ends 246 and 248. Extending from end 246 of forming tongue member 240 is the gas manifold member 249. The manifold member 249 has connection 250 in communication with gas passage 252 contained in member 240. Discharge opening 255 extends through the top 242 and is in fluid communication with passage 252. Discharge opening 242 is in alignment with cavity 207 of die member 200. The end 246 of tongue member 240 is fixedly mounted to the top 232 of tower member 230 such that the member 240 extends in a cantilevered fashion between the top 178 of plate member 170 and the bottom 197 of top plate member 190, and over extension member 180.

The machine 100 of the present invention operates in the following manner to form cavities in pouches utilizing the process of the present invention. As seen in the FIGS. 2-8, an operator faces the side of the machine 100 opposite the side where the mounting tower 230 is located, and facing free end 248 of forming tongue member 240. In the starting position, the actuating cylinders 160 and 220 move the plates 170 and 190 downwardly and upwardly, respectively, to form an opening about the forming tongue member 240. The operator then takes a pouch 10 and moves the top side 15 and entrance opening 20 over the free standing end 248 of the tongue member 240 and slides the pouch 10 onto section 242 until the end 15 of the pouch 10 engages or is proximal to the free end 248 of tongue member 240, and tongue member 240 is contained in part in interior cavity 22 of pouch 10. The operator then actuates the cylinders 160 and 220 to move the plates 170 and 190 upwardly and downwardly, respectively, so that the top side 178 of plate 170 is in contact with the bottom sheet 40 of pouch 10 pressing it against the bottom of tongue member 240 and die member 200 is in contact with a section of the top sheet 30 of pouch 10 pressing it against the top of and tongue member 240. The operator then actuates a pressurized fluid supply such as air connected to manifold 248 causing the air to flow through the passage 252 in member 248 and exit through second opening 255 thereby pushing and forming the section of the top sheet 30 engaged between the side walls 202 and 204 of die member 200 into the cavity 207 of die member 200 thereby forming cavity 60 in sheet 30 of pouch 10, having substantially the shape of cavity 207. The operator then actuates the cylinders 160 and 220 to reverse their movement to pull plates 170 and 190 away from each other such that there is an opening about the tongue member 240. The operator then removes the pouch 10 having cavity 60 from tongue member 240, and proceeds to repeat the operation to form cavities in unformed pouches 10.

Although this invention has been shown and described with respect to detailed embodiments thereof, it will be understood by those skilled in the art that various changes in form and detail may be made without departing from the spirit and scope of the claimed invention.

What is claimed is:

1. A method for forming a cavity in a pouch having three sealed sides, comprising:
  A. providing a pouch comprising two sheets aligned and sealed along three sides such that the pouch has an unsealed side and an opening into an interior cavity;
  B. providing an apparatus comprising
    a frame;
    a bottom clamp plate member slidably mounted to the frame, said bottom plate having a top side and a bottom side, the bottom clamp plate member moveable between a first position and a second position;
    a top die plate member slidably mounted to the frame, said top plate having a top side and a bottom side, the top die plate member moveable between a first position and a second position;
    first and second actuators for moving the bottom clamp plate and the top die plate member toward each other;
    a die extending from the bottom of the top die plate member, said die having a cavity;
    a mounting tower member having a top and a bottom, the bottom of the tower member mounted to the frame;
    a tongue plate member having a first end and a second end, the plate member having a substantially flat planar top and substantially flat planar bottom, the second end fixedly mounted to the top of the tower member and the tongue member extending between the top plate member and the bottom plate member, the tongue member having a fluid passage having a first opening and a second opening through the top side, wherein the second opening is in substantial alignment with the cavity of the die, said first and second openings in communication with the fluid passage;
  C. placing the pouch over the tongue member, such that a section of the tongue is contained within the interior of the pouch;
  D. moving the top and bottom plate members toward each other such that the die contacts the top of the pouch and the bottom plate member contacts the bottom of the pouch against the bottom and top surfaces of the tongue member, respectively;
  E. causing a pressurized fluid to move into the fluid passage of the tongue member and out through the opening, thereby causing a section of the top sheet of the pouch to be forced into the cavity of the die, thereby forming a cavity in the top sheet of the pouch.
  F. moving the top and bottom plate members away from the tongue member; and,
  G. removing the pouch having a formed cavity from the tongue member.

* * * * *